US012649065B2

(12) United States Patent
Ibanez

(10) Patent No.: US 12,649,065 B2
(45) Date of Patent: Jun. 9, 2026

(54) IMPLANTABLE MEDICAL DEVICE WITH CIRCULAR FEEDTHROUGH AREA

(71) Applicant: Cochlear Limited, Macquarie University (AU)

(72) Inventor: Hervé Ibanez, Vallauris (FR)

(73) Assignee: Cochlear Limited, Macquarie University (AU)

( * ) Notice: Subject to any disclaimer, the term of this patent is extended or adjusted under 35 U.S.C. 154(b) by 285 days.

(21) Appl. No.: 18/490,775

(22) Filed: Oct. 20, 2023

(65) Prior Publication Data

US 2024/0139529 A1 May 2, 2024

(30) Foreign Application Priority Data

Oct. 26, 2022 (EP) .................................... 22203839

(51) Int. Cl.
*A61N 1/375* (2006.01)
(52) U.S. Cl.
CPC .................................. *A61N 1/3754* (2013.01)
(58) Field of Classification Search
CPC .... A61N 1/3754; A61N 1/3752; A61N 1/375; A61N 1/3605; A61N 1/362; A61N 1/36038; A61N 1/36036; A61N 1/37512; A61N 1/37514; A61N 1/3758; A61N 1/08; A61N 1/086; A61N 1/18; A61N 1/37223; A61N 1/0541; A61N 1/37229
See application file for complete search history.

(56) References Cited

U.S. PATENT DOCUMENTS

| | | | | | |
|---|---|---|---|---|---|
| 5,272,283 | A | * | 12/1993 | Kuzma | A61N 1/3754 |
| | | | | | 174/262 |
| 8,135,474 | B1 | | 3/2012 | Xie | |
| 2011/0059331 | A1 | * | 3/2011 | Smith | B23K 1/18 |
| | | | | | 428/596 |
| 2015/0000882 | A1 | | 1/2015 | Yang | |
| 2015/0273219 | A1 | * | 10/2015 | Perraud | A61N 1/3754 |
| | | | | | 607/116 |
| 2020/0121934 | A1 | * | 4/2020 | Ibanez | H01R 13/5224 |

FOREIGN PATENT DOCUMENTS

EP          3639889          4/2020

* cited by examiner

*Primary Examiner* — Carl H Layno
*Assistant Examiner* — Anh-Khoa N Dinh
(74) *Attorney, Agent, or Firm* — Edell, Shapiro & Finnan, LLC

(57) ABSTRACT

An implantable medical device includes a sealed flat housing enclosing an electronic circuitry; a recess area formed on a side surface of the housing; at least one feedthrough area protruding from the recess area; at least one feedthrough area protruding from the recess area; and a plurality of feedthrough conductors cumulated on said feedthrough area, each feedthrough conductor comprising a proximal end part connected to the enclosed electronic circuitry and a distal end part extending from said feedthrough area.

20 Claims, 3 Drawing Sheets

IMPLANTABLE MEDICAL DEVICE WITH CIRCULAR FEEDTHROUGH AREA

FIELD

The present disclosure relates to implantable medical devices. More particularly, the disclosure relates to implantable devices with electrical contacts where electrical wires are attached like cochlear implants, heart pacemakers, or brain stimulating devices. The electrical wires are connected to an electrode that serves for sensing and/or stimulating a bodily part such as a cochlea, a heart muscle, or a particular area of the brain.

BACKGROUND

Implanted medical devices utilize hermetically sealed housings to isolate the device from the body environment. Such devices require that electrical signals are passed from within the housing to external connectors or vice-versa while maintaining hermetical tightness of the housing. Depending upon the configuration of the implantable device, there may be multiple electrical paths required between an electronic circuitry enclosed within the housing and the external electrical contacts. These paths are usually electrically and mechanically integrated with the device in order to provide a safe, long-term arrangement that does not compromise hermetic housing.

Many devices use feedthrough conductors to transfer electrical signals between the inside of the hermetically sealed housing and the outside of said housing. The distal end parts of the feedthrough conductors are available externally to the housing and serve as contact portion for the electrodes that are implanted in a tissue of a bodily part.

Conventionally, the electrical connection between feedthrough conductors and the electrode is made by positioning a plurality of connectors over a non-conductive unit, thereby connecting one end of each connector to a corresponding feedthrough conductor. The other end of each connector is guided towards the outer periphery of the housing.

During the manufacturing of the device, and later, during the implantation, an impact may be applied to the device. As the non-conductive unit is in an exposed position, protruding at a side of the housing, the non-conductive unit is sensible to any external impact. Such an impact may involve a pull-out force applied to the feedthrough conductors extending through the non-conductive unit in a direction away from the housing. Due to the conventional rectangular shape and the ceramic material of the non-conductive unit, this part is little robust to mechanical loads, e.g. applied in its center, which lead to flexural stress and damages on it. The result of this damages may be low reliability and even leakage of the device.

Therefore, there is a need to provide a solution that addresses at least some of the above-mentioned problems.

SUMMARY

According to an aspect, an implantable medical device is disclosed. The implantable medical device may include a sealed flat housing that encloses an electronic circuitry, a recess area formed on a side surface of the housing, at least one feedthrough area protruding from the recess area and a plurality of feedthrough conductors cumulated on said feedthrough area. Each feedthrough conductor may comprise a proximal end part connected to the enclosed electronic circuitry and a distal end part extending from the feedthrough area.

The feedthrough conductors may be connected to wires that are arranged at the outer peripheral surface of the housing. In particular, the feedthrough conductors may extend from the at least one feedthrough area protruding from the recess area on the side surface of the housing to ensure a reliable connection to the wires. However, the feedthrough conductors could also be flat so as to be flush with the surface of the feedthrough area which may be essentially parallel to the side surface of the housing. With their respective other end, the wires may be connected to an electrode.

The at least one feedthrough area may have a substantially circular shape. This is particularly advantageous in view of mechanical stresses applied to the implantable medical device, in particular on the at least one feedthrough area protruding from the recess area of the housing. Impacts may be particularly be applied to the center of the feedthrough area, such as tension on the feedthrough conductors via the wires connected to the electrode. The substantially circular shape of the at least one feedthrough area may allow for increasing the robustness of the feedthrough area regarding flexural constrains. In particular, the surface of the feedthrough area which is substantially parallel to the side surface of the housing may have a circular shape. The surface of the feedthrough area exposed to mechanical impacts may thus be decreased compared to known shapes such as of substantially rectangular feedthrough areas.

In an embodiment, the plurality of feedthrough conductors may be at least partially arranged substantially concentrically on the at least one feedthrough area. In particular, the plurality of feedthrough conductors may be arranged at least partly symmetrically around the center of the substantially circular feedthrough area. This may particularly allow for an enlarged clearance between the feedthrough conductors. The two-dimensional arrangement on the feedthrough area allows for reasonable spacing between the feedthrough conductors and benefits establishing reliable connections (e.g. weld connections), even though the feedthrough conductors are closely concentrated in a small area. The feedthrough conductors may be arranged in an array or distributed randomly on said feedthrough area.

In an embodiment, the at least one feedthrough area may comprise a substantially circular non-conductive component having a plurality of feedthrough holes. The plurality of feedthrough conductors may at least partially extend through said feedthrough holes of the non-conductive component. Accordingly, the feedthrough holes of the non-conductive component may also be arranged at least partially concentrically.

The feedthrough holes may extend from a lower surface of the non-conductive component, e.g. the surface facing the electronic circuitry, to an upper surface of the non-conductive component, e.g. the surface from which the feedthrough conductors are protruding, with an essentially uniform diameter, e.g. a diameter slightly bigger than the outer diameter of the feedthrough conductors. It is also conceivable that the diameter of the feedthrough holes varies. While, for example, the feedthrough holes may mainly have a diameter slightly bigger than the diameter of the feedthrough conductors, the diameter may be enlarged close to the upper surface where the feedthrough conductors may be connected to the wires, e.g. via connectors, for example, by welding or brazing.

Preferably, the non-conductive component comprises a surface area of less than 20 mm$^2$, particularly less than 15 mm$^2$, more particularly 9 mm 2 to 11 mm$^2$. In particular, the upper surface of the non-conductive component may comprise a surface area of less than 20 mm$^2$, particularly less than 15 mm$^2$, more particularly 9 mm 2 to 11 mm$^2$. The surface area may, for example, be between 10 mm 2 to 11 mm$^2$, in particular around 10 mm$^2$. The surface of the feedthrough area which is exposed to mechanical impacts is thus relatively small and less susceptible to mechanical impacts compared to feedthrough areas known from the prior art.

In an embodiment, the non-conductive component may comprise an electrically insulating material. In particular, the non-conductive component may comprise a ceramic material, more particularly alumina.

In an embodiment, the implantable medical device comprises at least two, in particular three, feedthrough areas protruding from the recess area. Each feedthrough area may comprise a substantially circular non-conductive component having a plurality of feedthrough holes.

Preferably, the total surface area of the non-conductive components of the feedthrough areas may be less than 40 mm$^2$, particularly less than 35 mm$^2$, more particularly 30 mm 2 to 33 mm$^2$.

In an embodiment, the implantable medical device may comprise at least one feedthrough ring configured to connect the at least one non-conductive component to the housing of the implantable medical device.

On the one hand, the at least one feedthrough ring may be connected to the housing of the implantable medical device. The connection between the housing and the feedthrough ring may be form-locking. To this end, the housing may comprise at least one through hole through which the feedthrough ring fits only partially. The feedthrough ring may thus only be covered partially when the housing is placed over the at least one feedthrough ring and sealed. In particular, the feedthrough ring may comprise at least one protruding portion and an outer shoulder. The outer should may have a bigger diameter than the through hole of the housing. The feedthrough ring may thus abut against the housing with this outer shoulder, when the housing is placed over the at least one feedthrough ring. The protruding portion of the feedthrough ring may be flush with the outer periphery of the housing when the feedthrough ring and the housing are connected.

On the other hand, the at least one feedthrough ring may be connected to the non-conductive component of the feedthrough area. To this end, the feedthrough ring may have an inner diameter which is slightly bigger than the outer diameter of the non-conductive component. The non-conductive component may thus be surrounded by the feedthrough ring. In particular, the non-conductive component may be protruding from the feedthrough ring.

In an embodiment of the present disclosure, the connection between the at least one non-conductive component and the at least one feedthrough ring may be hermetically sealed. In particular, the connection between the at least one non-conductive component and the at least one feedthrough ring may be sealed by a brazing seal. To this end, a feedthrough brazing ring may be place on top of the surface of the feedthrough ring pointing to the outer periphery of the housing and used for sealing, in particular hermetically sealing, the connection between the at least one feedthrough area and the at least one feedthrough ring. The feedthrough ring may have an inner diameter which is slightly bigger than the outer diameter of the non-conductive material. With the brazing ring, a brazing seal may be provided between the feedthrough ring and the non-conductive component and thus hermetically seal the connection.

The implantable medical device may further comprise a plurality of connectors configured to provide connections between the plurality of feedthrough connectors and a plurality of wires. Each connector may comprise a first end section adapted to be connected with a feedthrough conductor and a second end section adapted to be connected with a wire. The plurality of connectors may be positioned over the non-conductive unit, thereby connecting one end of each connector to a corresponding feedthrough conductor. The other end of each connector is guided towards the outer periphery of the housing. The connectors may be used as a terminal to facilitate the connection between the wire and the feedthrough conductor, for example in a soldering or welding process.

In an embodiment, the implantable medical device may comprise a tubing that houses the plurality of wires connected to said feedthrough conductors and that is arranged on the housing. The tubing may be used to house the plurality of wires. The tubing provides protection for the wires against external impacts. During manufacturing, the tubing allows guiding the wires commonly and facilitates the assembly step of connecting the wires to the feedthrough conductors. The tubing may be arranged on said housing so as to allow each wire to be connected with a feedthrough conductor.

In an embodiment, the implantable medical device further comprises a wire guide arranged on said side surface of the housing. In the wire guide, a plurality of guide grooves are formed for guiding the wires. This ensures that the wires are safely guided from their respective exit position at the tubing to the connection position at the feedthrough conductor. In particular, a wire guide, in which a plurality of guide grooves for guiding the wires are formed, is arranged on a side surface of the housing.

The wire guide may be made from an electrically insulating material. This ensures that the wires are housed electrically insulated from each other and from the housing. A risk of short circuit is thereby reduced.

The tubing may run along the outer periphery of the wire guide. For example, the tubing may be arranged to run around an outline of the wire guide so as to form a loop around the wire guide. However, the tubing can also be arranged along a part of the periphery of the wire guide. With the tubing running along the outer periphery of the wire guide, the contact surface between both members is increased. In particular, a tubing that runs around curves and corners of the wire guide has an increased wrap angle around the wire guide. This has the effect that the friction between the tubing and the wire guide is increased and thereby the mechanical stability of both parts relative to each other is increased. For example, if a pull-out force is applied to the tubing, the resistance against displacement of the tubing relative to the wire guide is increased without requiring additional fixing members and space. Thereby, the reliability of the electrical connections is increased, as the wires or the connections of the wires are less likely to break in case of an external mechanical impact.

The wire guide may have a hole through which the distal end part of the feedthrough conductor is exposed. Depending on the arrangement of the feedthrough conductors, each feedthrough conductor may be exposed through a separate hole or more than one feedthrough conductors may be exposed through a common hole. This enables that the areas around the feedthrough conductors, such as a housing surface, are covered by the wire guide and, therefore, protected. Consequently, it is facilitated to connect only the distal end part of the feedthrough conductor, which is the relevant part for making an electrical connection, with the wire. A risk for creating a short circuit between the wire and a part other than the feedthrough conductor is reduced and leads to a better reliability. In particular, in case the connection between the wire and the feedthrough conductor is made by material addition, such as welding or soldering, it is prevented that the added material spreads unintentionally.

A first end of each guide groove may communicate with an outer periphery of the wire guide and a second end of each guide groove may communicate with the feedthrough conductor. Thereby, the part of the wire outside the tubing may be housed in the guide groove along its whole length across the wire guide. This ensures protection of the wire. Further, by guiding each wire in a separate groove towards the feedthrough conductor, the risk of erroneously connecting a wire to another feedthrough conductor than the predetermined one is reduced.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other embodiments. These and other embodiments, features and/or technical effect will be apparent from and elucidated with reference to the illustrations described hereinafter in which:

DETAILED DESCRIPTION

Figure 1:
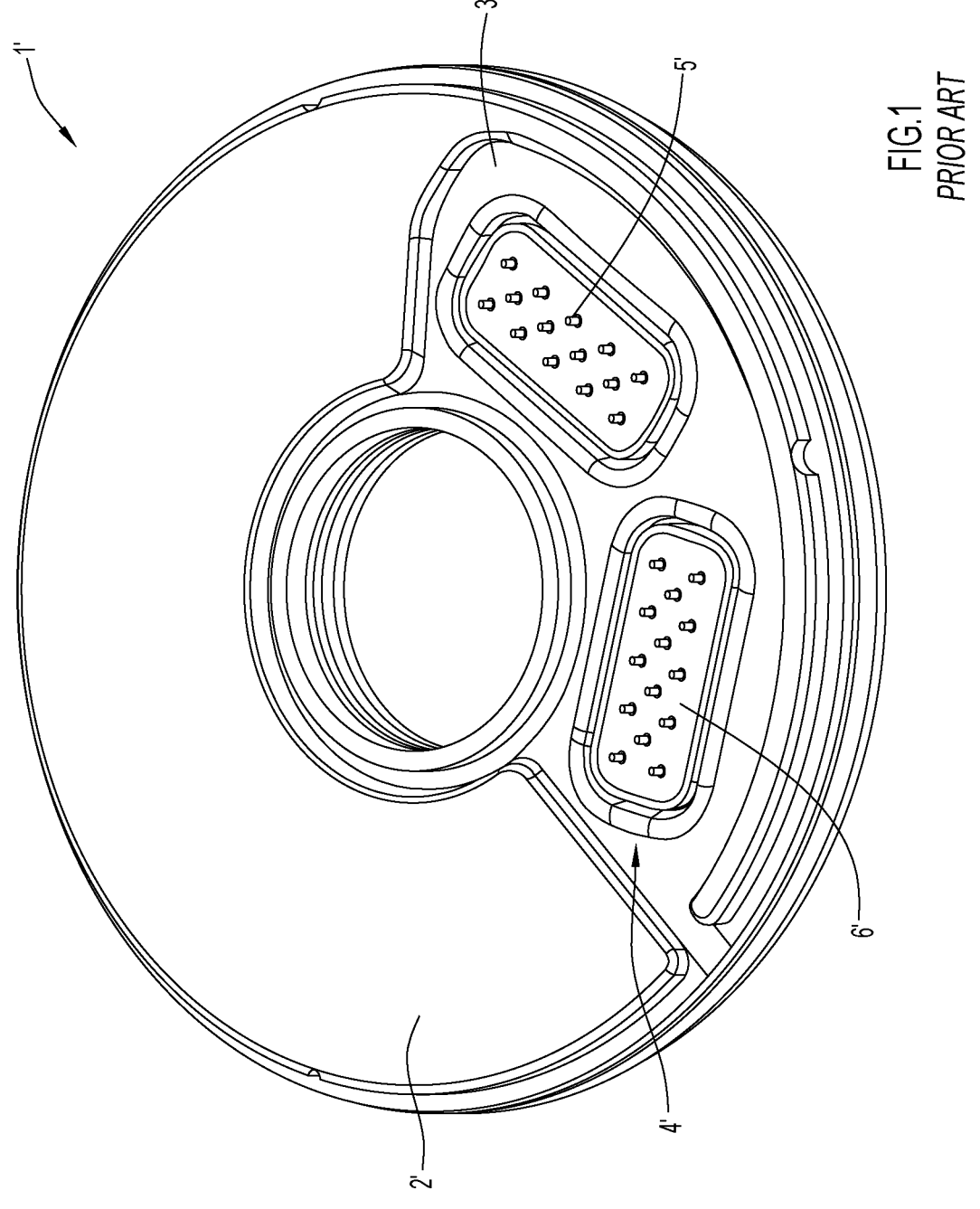
FIG. 1 illustrates an implantable medical device according to the prior art.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a smartphone or other electronic device, the smartphone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

It is intended that the structural features of the devices described above, either in the detailed description and/or in the claims, may be combined with steps of the method, when appropriately substituted by a corresponding process.

FIG. 1 illustrates an implantable medical device 1' according to the prior art. The implantable medical device 1' includes a sealed housing 2' that encloses an electronic circuitry. A recess area 3' is formed on one side surface of the housing 2'. In the recess area 3' two feedthrough areas 4' are protruding and a plurality of feedthrough conductors 5' are extending from each feedthrough area 4'.

Each feedthrough area 4' has a substantially rectangular shape with rounded corners and comprises a non-conductive component 6' of the same shape. The feedthrough conductors 5' are arranged in three rows, wherein the two outer rows each comprise five feedthrough conductors 5' spaced apart from each other. The middle row comprises four feedthrough conductors 5' spaced apart from each other, which are jointly shifted in a direction in which the row extends. While each non-conductive component 6' comprises a surface area of 21.7 mm$^2$, in total, the non-conductive components 6' have a surface area of 43.4 mm$^2$.

Figure 2:
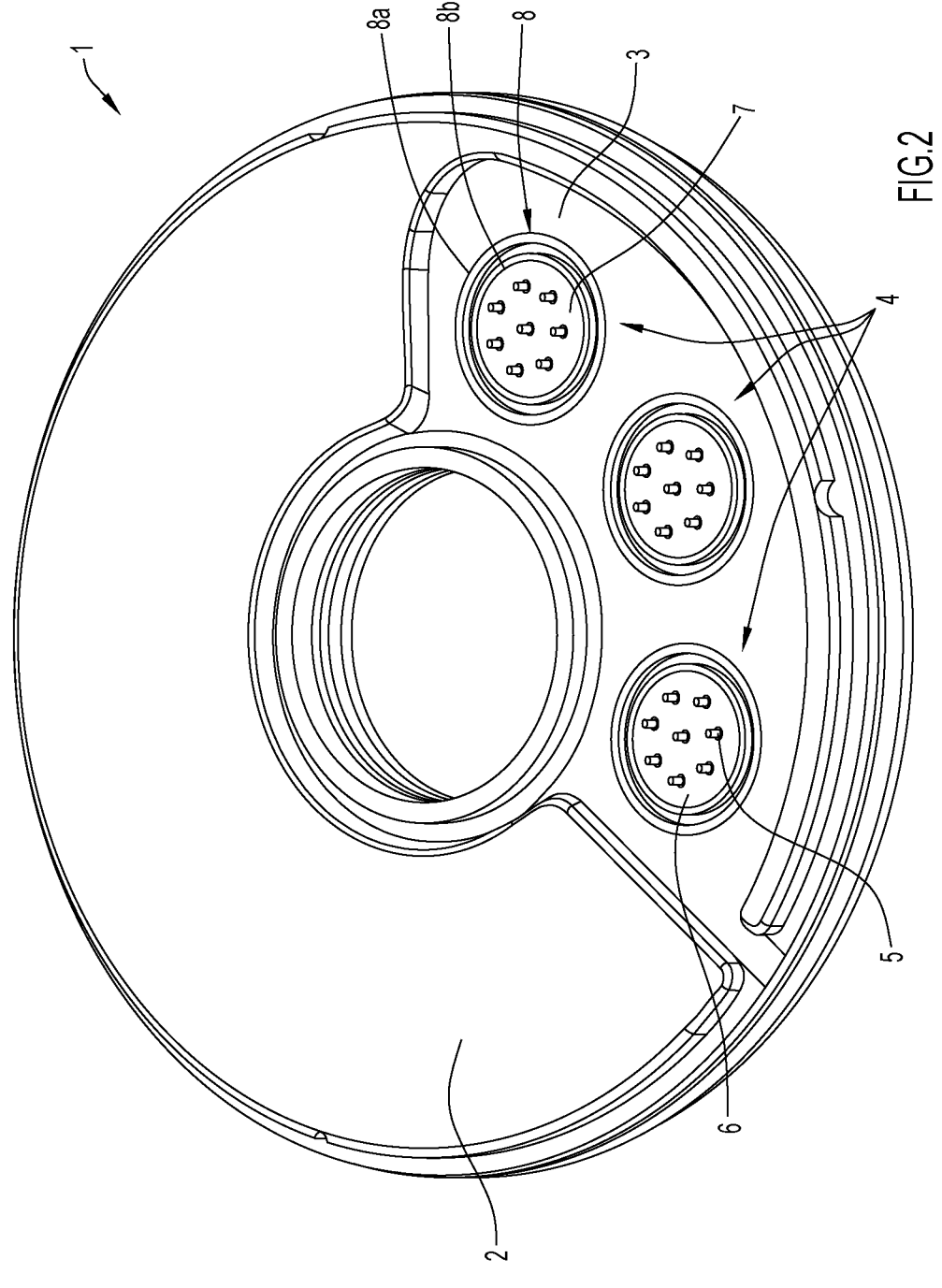
FIG. 2 illustrates an implantable medical device according to an embodiment.

FIG. 2 illustrates an implantable medical device 1 according to an embodiment of the present disclosure.

The implantable medical device 1 is e.g. a part of a cochlear implant comprising an external device and the implantable medical device 1, the implantable medical device 1 comprising a multi-electrode array.

The implantable medical device 1 includes a sealed housing 2 that encloses an electronic circuitry. The housing 2 is flat and has a circular outline in a plan view. When viewed in said plan view, the housing 2 further has a circular through hole arranged concentrically to the circular outline of the housing 2. Thereby, two side surfaces with the shape of a circular ring are formed on each side of the housing 2.

A recess area 3 is formed on one side surface of the housing 2. In the recess area 3 three feedthrough areas 4 are protruding. Each feedthrough area 4 has a substantially circular shape and comprises a non-conductive component 6. Each non-conductive component 6 also has a substantially circular shape and is surrounded by a feedthrough ring 8. The feedthrough rings 8 are configured to connect the non-conductive components 6 to the housing 2. To this end, the feedthrough rings 8 comprise at protruding portions 8a, 8b and an outer shoulder (not shown). The outer shoulder of the feedthrough rings 8 abuts against the inner surface (not shown) of the housing 2, while the protruding portions 8a, 8b are flush with the recess area 3 of outer periphery of the housing 2. To hermetically seal the connection between the at least one non-conductive component 6 and the at least one feedthrough ring 8, a brazing seal (not shown) is provided.

Each non-conductive component 6 comprises a surface area of 10.2 mm$^2$. In total, the non-conductive components 6 of the three feedthrough areas 4 have a surface area of 30.6 mm$^2$. Accordingly, the total surface of the non-conductive components 6 is reduced of approximately 30% compared to the implantable medical device 1' according to the prior art, as shown in FIG. 1. The surface of the non-conductive components 6 being exposed to an impact is thus significantly reduced.

The non-conductive components 6 of the implantable medical device 1 each comprise a plurality of feedthrough holes 7. A plurality of feedthrough conductors 5 at least partially extends through said feedthrough holes 7. The plurality of feedthrough conductors 5 are thus cumulated on each feedthrough area 4. In particular, the feedthrough conductors 5 are arranged substantially concentrically on each feedthrough area 4. While seven feedthrough conductors 5 are arranged concentrically with equal distance to the outer edge of each non-conductive component 6 and spaced apart equally, one feedthrough conductor 5 is positioned in the center of each circular non-conductive component 6, also having substantially the same spacing to all other feedthrough conductors 5 of the same non-conductive component 6. Thereby, the clearance between the feedthrough conductor 5 in the center and the feedthrough conductors 5 on the outer circle is enlarged.

Each feedthrough conductor 5 of the plurality of feedthrough conductors 5 comprises a proximal end part (not shown) connected to the enclosed electronic circuitry and a distal end part available externally to the housing 2. Each distal end part has a cylindrical shape and extends from the feedthrough area 4, in particular the non-conductive component 6.

Figure 3:
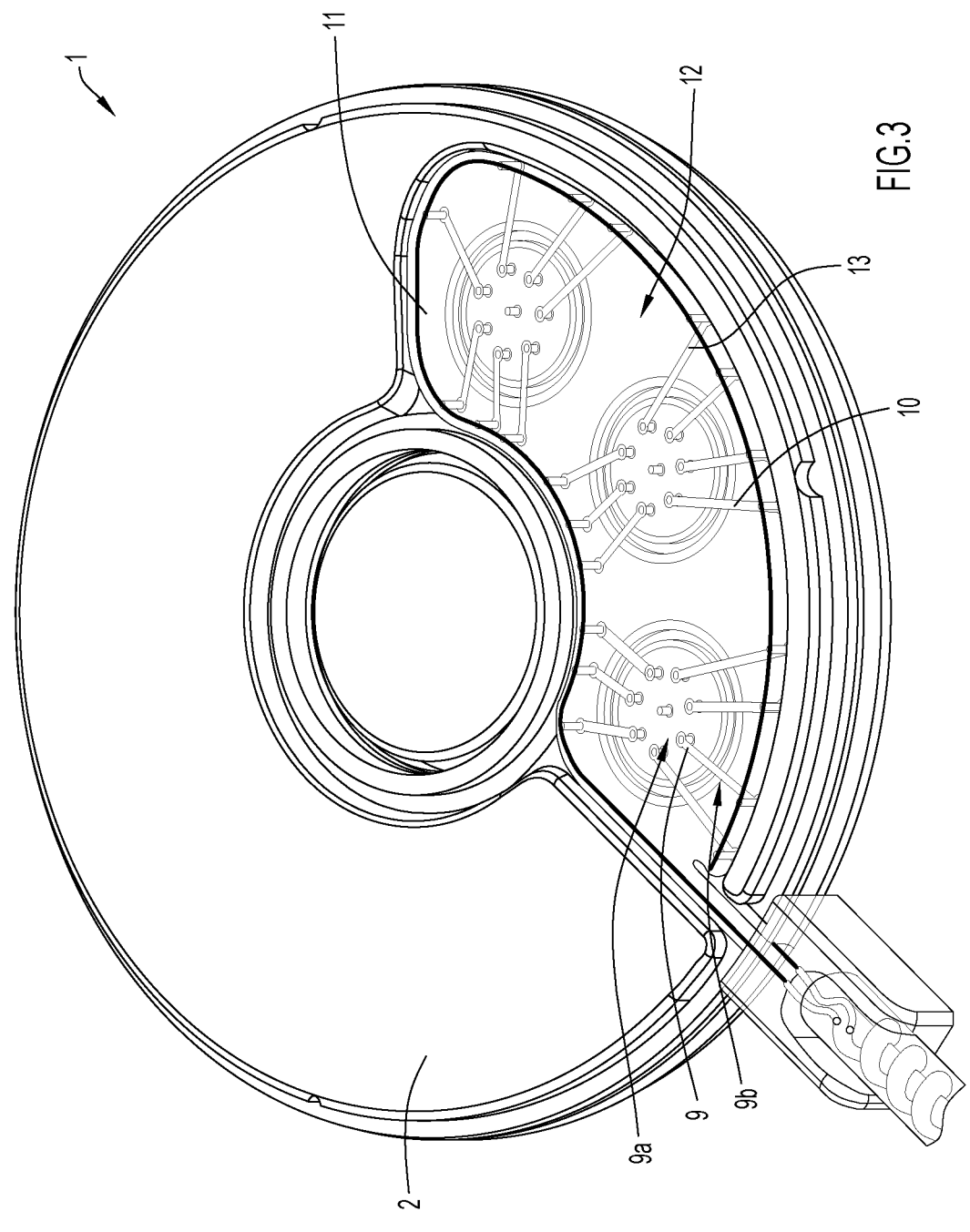
FIG. 3 illustrates an implantable medical device according to another embodiment.

FIG. 3 illustrates an implantable medical device 1 according to another embodiment of the present disclosure.

The implantable medical device 1 is e.g. a part of a cochlear implant comprising an external device and the implantable medical device 1, the implantable medical device 1 comprising a multi-electrode array.

The implantable medical device 1 comprises a tubing 11. The tubing 11 has a tubular shape and is made of a flexible material so that it can be bent along its longitudinal axis. One end of the tubing 11 extends from the housing 2 towards the electrodes of the implantable medical device 1 in a radial direction of the circular outline of the housing 2.

The other end of the tubing 11 is arranged on a side surface of the housing 2 and, due to several bends, guided along the periphery of the recess area 3. The tubing 11 is thereby forming a closed loop around the plurality of feedthrough conductors 5 so that an axial end surface of the tubing 11 abuts against the outer peripheral surface of said tubing 11. Alternatively, the tubing 11 may be guided along only a part of the recess area 3 without the axial end face of the tubing 11 abutting against the outer peripheral surface of said tubing 11.

At the inside of the tubing 11, a plurality of electrical wires 10 is housed. At the one end of the tubing 11 extending from the housing 2, twenty-one wires 10 are running jointly inside the tubing 11 towards the electrodes of the implantable medical device 1, while maintained electrically insulated. At the other end of the tubing 11 arranged on the housing 2, one the wires 10 passes through a respective slit in the tubing 11 in order to extend from the tubing 11 towards a respective feedthrough conductor 5, to which it is to be connected.

The implantable medical device 1 further comprises a wire guide 12 arranged on a side surface of the housing 2. The wire guide 12 is made of an electrically non-conductive material in order to provide electrical insulation for the surrounding members.

The wire guide 12 is arranged in the recess area 3 of the side surface of the housing 2 and the shape of the wire guide 12 corresponds to the shape of the recess area 3. A height of the wire guide 12 corresponds to a depth of the recess area 3 so that the upper surface of the wire guide 12 is substantially flush with the surrounding part of the side surface of the housing 2.

The wire guide 12 is arranged inside the loop formed by the tubing 11 so that the tubing 11 abuts against an outer periphery of the wire guide 12. A plurality of guide grooves 13 are formed in the wire guide 12 in order to guide the electrical wires 10 extending from the tubing 11. The number of guide grooves 13 corresponds to the number of wires 10 in order to guide each wire 10 electrically insulated in a separate guide groove 13. Each guide groove 13 is open towards the same side of the wire guide 12.

A first end of each guide groove 13 is arranged close or communicates with a respective slit of the tubing 11 through which a wire 10 is passed. A second end of each guide groove 13 communicates with a feedthrough hole 7 of a non-conductive component 6 through which a respective feedthrough conductor 5 is exposed. Thereby, each wire 10 is guided in the wire guide 12 from the wire 10 exit position at the tubing 11 to the feedthrough conductor 5, to which it is to be connected.

A plurality of spatially separated connectors 9 are configured to provide terminal connections for the plurality of electrical wires 10. Each connector 9 serves as a link between a wire 10 and a feedthrough conductor 5, thereby providing an electrical connection. The connectors 9 are attached to the wires 10 by electrical welding. The connection between the connectors 9 and the feedthrough conductors 5 is made by laser welding. Alternatively, the connections may be made by other joining methods such as soldering, clamping, screwing, or riveting.

A final overmolding (not shown) is applied to cover the housing 2, the tubing 11, the wire guide 12 and the connections between the wires 10 and the feedthrough conductors 5.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An implantable medical device comprising:
   a sealed flat housing enclosing an electronic circuitry and comprising a central hole;
   a recess area formed on a side surface of the housing, wherein the recess area comprises a recess surface;
   a plurality of feedthrough areas formed into the recess surface, wherein each feedthrough area of the plurality of feedthrough areas comprises a non-conductive component forming a substantially circular shape, and the recess surface separates each feedthrough area of the plurality of feedthrough areas from one another, and the plurality of feedthrough areas at least partially surrounds the central hole;

a plurality of feedthrough conductors cumulated on each feedthrough area of the plurality of feedthrough areas, each feedthrough conductor of the plurality of feedthrough conductors comprising a proximal end part connected to the electronic circuitry and a distal end part extending from said feedthrough area, and the plurality of feedthrough conductors circumferentially surround a center of a corresponding non-conductive component of its feedthrough area; and a plurality of wires connected to the plurality of feedthrough conductors, wherein each wire of the plurality of wires extends over the recess surface.

2. The implantable medical device according to claim 1, wherein the plurality of feedthrough conductors comprises seven feedthrough conductors for each feedthrough area.

3. The implantable medical device according to claim 1, wherein the non-conductive component of each feedthrough area of the plurality of feedthrough areas has a plurality of feedthrough holes, wherein the plurality of feedthrough conductors at least partially extends through said plurality of feedthrough holes.

4. The implantable medical device according to claim 1, wherein each non-conductive component comprises a surface area of less than 20 mm$^2$.

5. The implantable medical device according to claim 1, wherein each non-conductive component comprises an electrically insulating material.

6. The implantable medical device according to claim 1, wherein the plurality of feedthrough conductors comprises at least two, in particular three, feedthrough areas.

7. The implantable medical device according to claim 1, wherein a total surface area of the non-conductive components of the plurality of feedthrough areas is less than 40 mm$^2$.

8. The implantable medical device according to claim 1, wherein each feedthrough area of the plurality of feedthrough areas further comprises a feedthrough ring surrounding the non-conductive component and connecting the non-conductive component with the housing of the implantable medical device, and the recess surface separates each feedthrough ring from one another.

9. The implantable medical device according to claim 8, wherein the non-conductive component and the feedthrough ring are hermetically sealed therebetween.

10. The implantable medical device according to claim 8, further comprising a plurality of connectors configured to provide connections between the plurality of feedthrough conductors and the plurality of wires, wherein each connector of the plurality of connectors comprises a first end section adapted to be connected with a feedthrough conductor of the plurality of feedthrough conductors and a second end section adapted to be connected with a wire of the plurality of wires.

11. The implantable medical device according to claim 1, further comprising a tubing that houses the plurality of wires connected to said plurality of feedthrough conductors and that is arranged on the housing.

12. The implantable medical device according to claim 1, further comprising a wire guide arranged on said side surface in which a plurality of guide grooves for guiding the wires are formed.

13. An implantable medical device comprising:

a housing enclosing an electronic circuitry and comprising a central hole;

a recess area formed into the housing and comprising a recess surface;

a plurality of non-conductive components formed into the recess surface, wherein each non-conductive component of the plurality of non-conductive components forms a substantially circular shape, and the recess surface separates each non-conductive component of the plurality of non-conductive components from one another, and the plurality of non-conductive components surrounds a portion of the central hole;

a plurality of feedthrough conductors, wherein each feedthrough conductor of the plurality of feedthrough conductors comprises a proximal end part connected to the electronic circuitry and a distal end part extending out of one of the plurality of non-conductive components, and the plurality of feedthrough conductors are arranged at the plurality of non-conductive components such that, at each non-conductive component of the plurality of non-conductive components, feedthrough conductors circumferentially surround a center of the non-conductive component;

a plurality of wires coupled to the plurality of feedthrough conductors, wherein each wire of the plurality of wires extends over the recess surface; and a plurality of connectors configured to provide connections between the plurality of feedthrough conductors and the plurality of wires, wherein each connector of the plurality of connectors comprises a first end section adapted to be connected with a feedthrough conductor and a second end section adapted to be connected with a wire, and each connector of the plurality of connectors extends over one of the plurality of non-conductive components.

14. The implantable medical device according to claim 13, wherein the plurality of non-conductive components circumferentially surround the portion of the central hole.

15. The implantable medical device according to claim 13, comprising a wire guide disposed on the recess surface and having a plurality of guide grooves, wherein each wire of the plurality of wires extends through one of the plurality of guide grooves to extend over the recess surface.

16. The implantable medical device according to claim 15, wherein the wire guide has a height such that an upper surface of the wire guide is substantially flush with the housing.

17. The implantable medical device according to claim 15, comprising tubing at least partially surrounding the wire guide, wherein the plurality of guide grooves guides the plurality of wires over the recess surface to the tubing.

18. The implantable medical device according to claim 13, wherein the plurality of non-conductive components comprises three non-conductive components.

19. The implantable medical device according to claim 13, comprising a plurality of feedthrough rings, wherein each feedthrough ring of the plurality of feedthrough rings surrounds a non-conductive component of the plurality of non-conductive components and connects the non-conductive component to the housing, and each connector of the plurality of connectors extends over a feedthrough ring of the plurality of feedthrough rings.

20. The implantable medical device according to claim 13, wherein, at each non-conductive component of the plurality of non-conductive components, a single row of feedthrough conductors circumferentially surrounds the center of the non-conductive component.

* * * * *